(12) United States Patent
Jung (10) Patent No.: US 6,457,180 B1
(45) Date of Patent: Oct. 1, 2002

(54) HEADGEAR FOR SHIELDING ULTRAVIOLET RAYS

(76) Inventor: Yong H. Jung, 2F Osan Bldg, Yonsan-9-dong, Yonjeku, Pusan (KR)

( * ) Notice: Subject to any disclaimer, the term of this patent is extended or adjusted under 35 U.S.C. 154(b) by 0 days.

(21) Appl. No.: 09/888,974

(22) Filed: Jun. 27, 2001

(51) Int. Cl.7 .................................................. A61F 9/02
(52) U.S. Cl. .................................................. 2/12; 2/424
(58) Field of Search .............................. 2/10, 12, 424; 128/857

(56) References Cited

U.S. PATENT DOCUMENTS 5,052,054 A * 10/1991 Birum ............................. 2/10
5,870,772 A * 2/1999 Sprouse ........................... 2/10

* cited by examiner

Primary Examiner—Peter Nerbun
Assistant Examiner—Katherine Moran
(74) Attorney, Agent, or Firm—John K. Park; Park & Sutton LLP (57) ABSTRACT

An ultraviolet rays shielding hat having a sun visor is disclosed. The hat includes an elastically circular band having an outer periphery, a plurality of guide supports attached to the side portions of the outer periphery, wherein said each guide support has a guide groove in each of a top side and a bottom side thereof, an inner support disk having an inner surface and an outer surface, wherein a slider is attached to the inner surface of the inner support disk and has a pair of guide rails inwardly extending therefrom, wherein the guide rails are slidably carried in the guide grooves, wherein a guide shaft extends from a central portion of the outer surface, and an outer support disk having a side engagement opening and a central engagement hole, wherein the guide shaft of the slider is rotatably engaged in the central engagement hole, wherein each side end of the sun visor is fixedly received in the side engagement opening.

8 Claims, 9 Drawing Sheets

HEADGEAR FOR SHIELDING ULTRAVIOLET RAYS

BACKGROUND OF THE INVENTION

The present invention relates to a hat with a sun visor to protect a user's face from ultraviolet rays of the sun during outdoor sports watching, beach outings, fishing and the like, especially, in summer. More specifically, this invention relates to a sun visor hat having a rolling device that enables a hinge portion linking a support band and the sun visor to make an adjustable movement so that the sun visor to the support band can be either vertically or horizontally adjusted, thereby effectively blocking the ultraviolet rays from the user's face.

A conventional sun visor hat constitutes a support band and a sun visor that are unitary with each other. In order to block the sun rays coming askew, the conventional hat needs to be turned to the side so that the sun visor can shield the sun rays.

According to another example of the conventional art, each side end of the sun visor is connected through a portion of the support band using a connection pin, where an elastic bushing is provided between the support band and the sun visor to prevent a fluctuation during a vertical movement. However, because each end of the sun visor rotating on the connection pin remains pushed up by the elastic bushing, the sun visor is not smooth in its vertical rotational movement.

Although a clearance between the bushing and the sun visor allows the vertical movement to become smooth, the sun visor tends to be lowered depending upon the user's head movement so that the user still reserves inconvenience in angular adjustment of the sun visor. A further inconvenience of the conventional sun visor hat is that the sun visor cannot be rotated side to side as the support band stays still.

SUMMARY OF THE INVENTION

The present invention is contrived to overcome the conventional disadvantages. Accordingly, it is an object of the present invention to provide a sun visor hat having a rolling device that enables a hinge portion linking a support band and the sun visor to make an adjustable movement so that the sun visor to the support band can be either vertically or horizontally adjusted, thereby effectively blocking the ultraviolet rays from the user's face.

To achieve the above-described object, a headgear for shielding ultraviolet rays according to the present invention comprises an elastically circular band having an outer periphery, wherein the outer periphery has side portions; a plurality of guide supports attached to the side portions of the outer periphery of the elastic band, wherein said each guide support has a guide groove in each of a top side and a bottom side thereof; an inner support disk having an inner surface and an outer surface, wherein a slider is attached to the inner surface of the inner support disk and has a pair of guide rails inwardly extending therefrom, wherein the guide rails are slidably carried in the guide grooves of the guide supports, wherein a guide shaft extends from a central portion of the outer surface of the inner support disk; and an outer support disk having a side engagement opening and a central engagement hole, wherein the guide shaft of the slider is rotatably engaged in the central engagement hole of the outer support disk, wherein each side end of the sun visor is fixedly received in the side engagement opening of the outer support disk.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

With reference to the accompanying drawings, a headgear for shielding ultraviolet rays according to the present invention will now be described.

As shown in FIGS. 1–6, a hat 1 according to an embodiment of the invention includes a sun visor 2 engaged to an elastic band 3. The elastic band 3 is formed in an open loop to facilitate wearing and taking off the hat 1. The open looped elastic band 3 has a thickness and a width. Along outer peripheral side portions of the elastic band 3 are mounted guide supports 110. Each guide support 110 has a groove 111. The bottom of the groove 111 is waved with a plurality of bossy protrusions 111a. Preferably, the groove 111 is formed in each of the upper surface and the lower surface of each guide support 110. In this construction, a sun visor unit 100 having the sun visor 2 is controllably engaged to the guide support 110.

The sun visor unit 100 includes a pair of inner disks 120 and a pair of outer disks 130. Each outer disk 130 is engaged to the corresponding inner disk 120. The outer disk 130 has a slider 124 formed on the inner surface thereof. An engagement opening 130a formed in a predetermined portion of the slider 124. The sun visor 2 is assembled into the engagement opening 130a of the slider 124.

The slider 124 includes a guide rail 125. The top surface portion of the guide rail 125 is waved to form bossy protrusions 125a so that when the slider 124 is movably carried on the guide support 110 the protrusions 111a, 125a may controllably cooperate with each other.

Meanwhile, a hinge shaft 121 extends from the outer surface of the inner disk 120. A hook opening 122 is formed in an outer peripheral portion of the hinge shaft 121. In the outer periphery are formed a plurality of openings 123 connected to each other to form a rugged circular groove.

An insertion hole 131 is formed in the inner surface of the outer disk 130. The inner surface of the outer disk 130 is radially divided into a plurality of elastic plates 132. On a portion of each elastic plate 132 is formed a protrusion 133 which fits in the circular groove 123 of the inner disk 120. As a result, each end portion of the sun visor 2 is held by the hinge shaft 121 that goes into the insertion hole 131, whereby the sun visor 2 makes vertical angular movements.

A hook protrusion 131a is formed in an inner peripheral portion of the insertion hole 131. So when the hinge shaft 121 of the inner disk 120 is inserted into the insertion hole 131 of the outer disk 130, the hook opening 122 in the hinge shaft 121 becomes controllably engaged to the hook protrusion 131a of the insertion hole 131.

Selectively, a closure 134 may be attached on the outer surface of the outer disk 130 so as to prevent the hinge shaft 121 from exposure for a decorative finishing.

Figure 1:
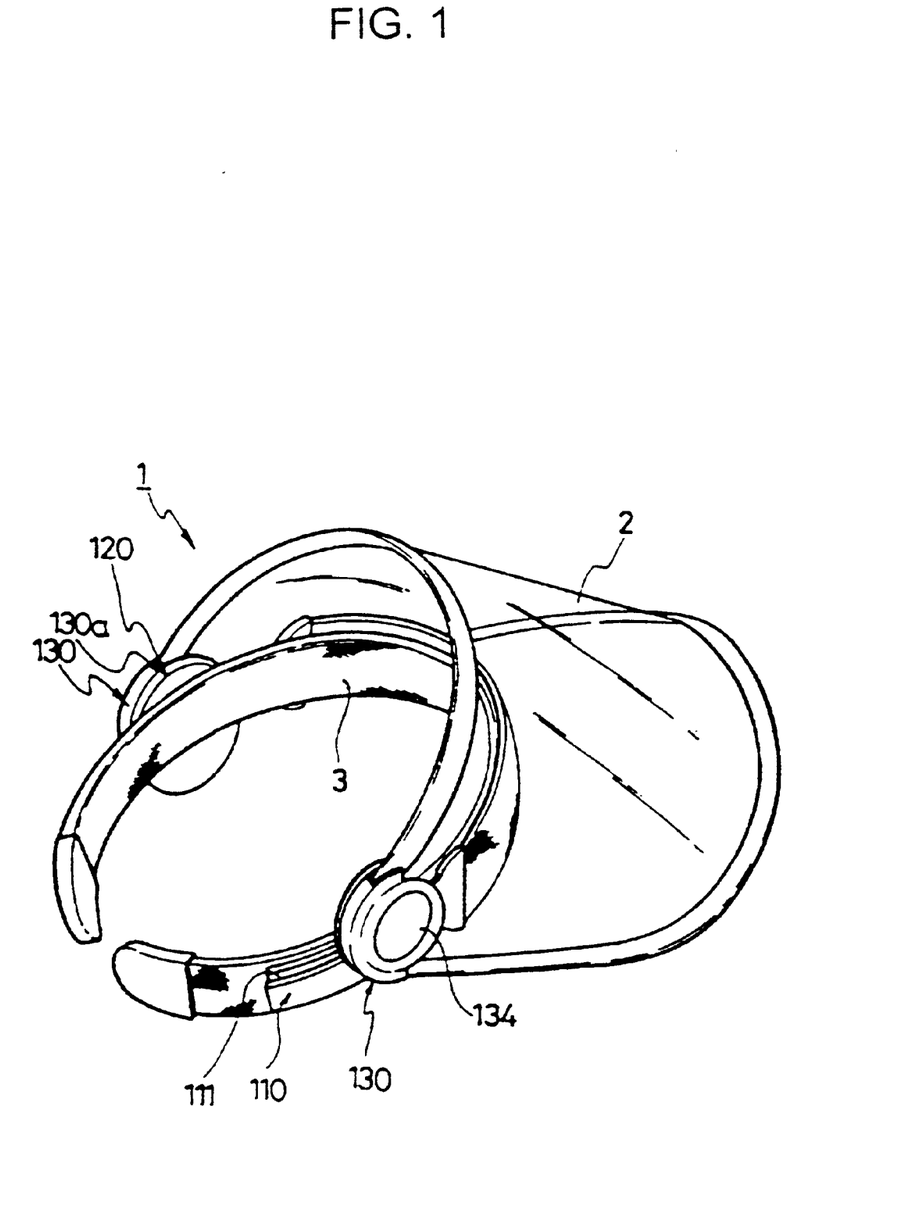
FIG. 1 is a perspective view of a hat shielding ultraviolet rays according to the present invention.
Figure 2:
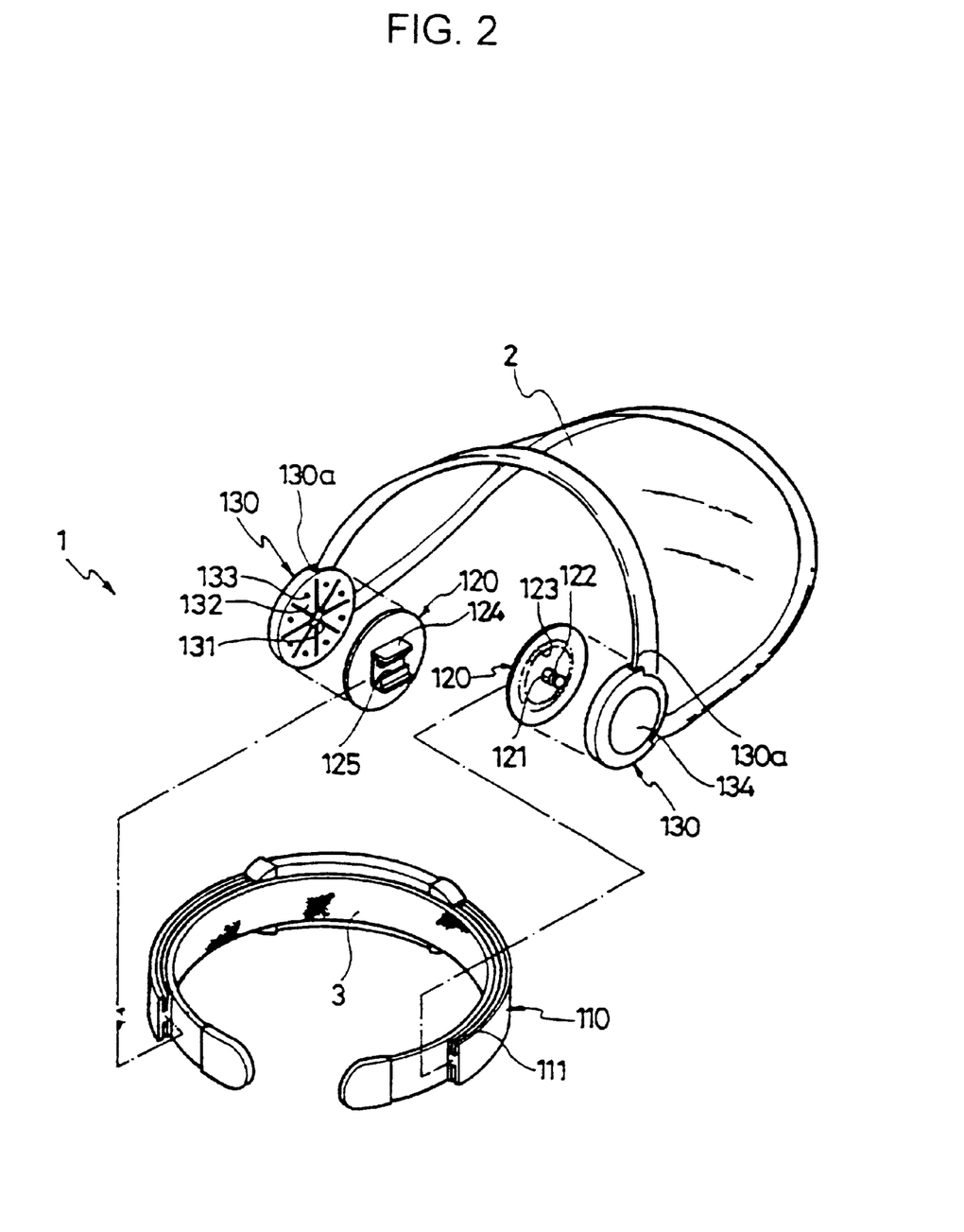
FIG. 2 is a partially exploded perspective view of a hat shielding ultraviolet rays according to the present invention.
Figure 3:
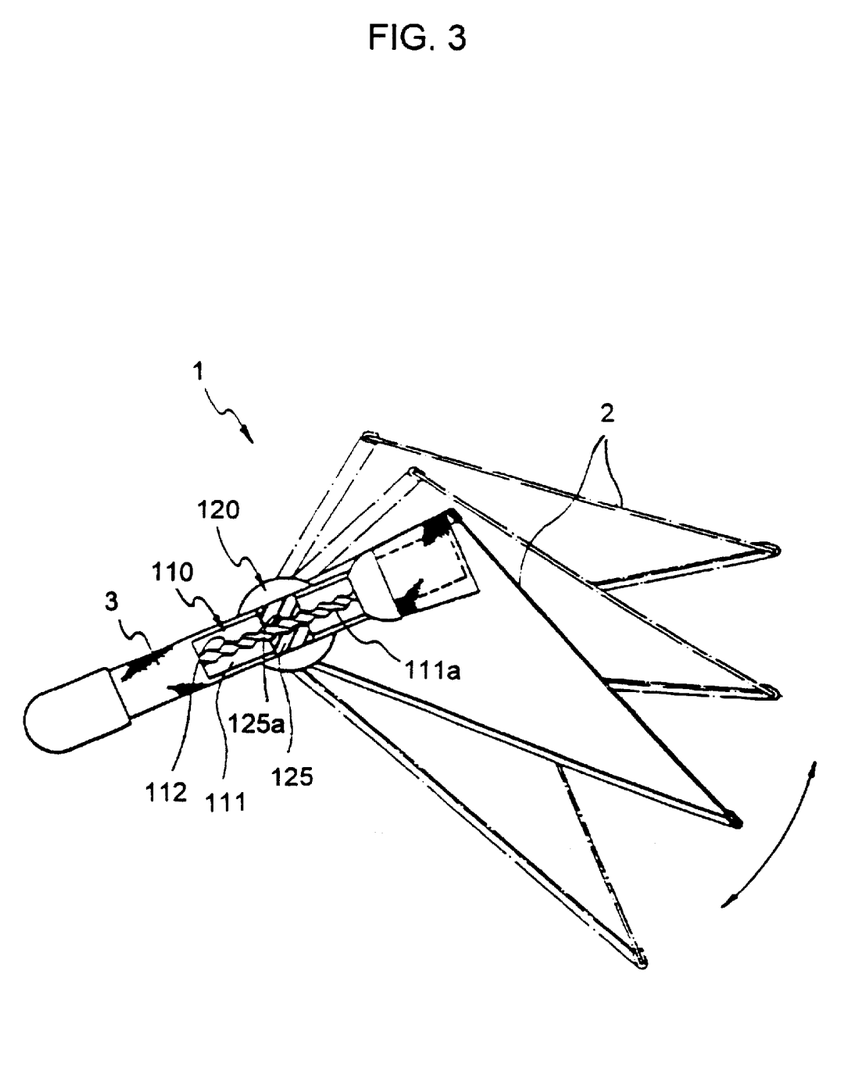
FIG. 3 is an operational view showing a vertical rotation of a sun visor to the hat according to the present invention.
Figure 4:
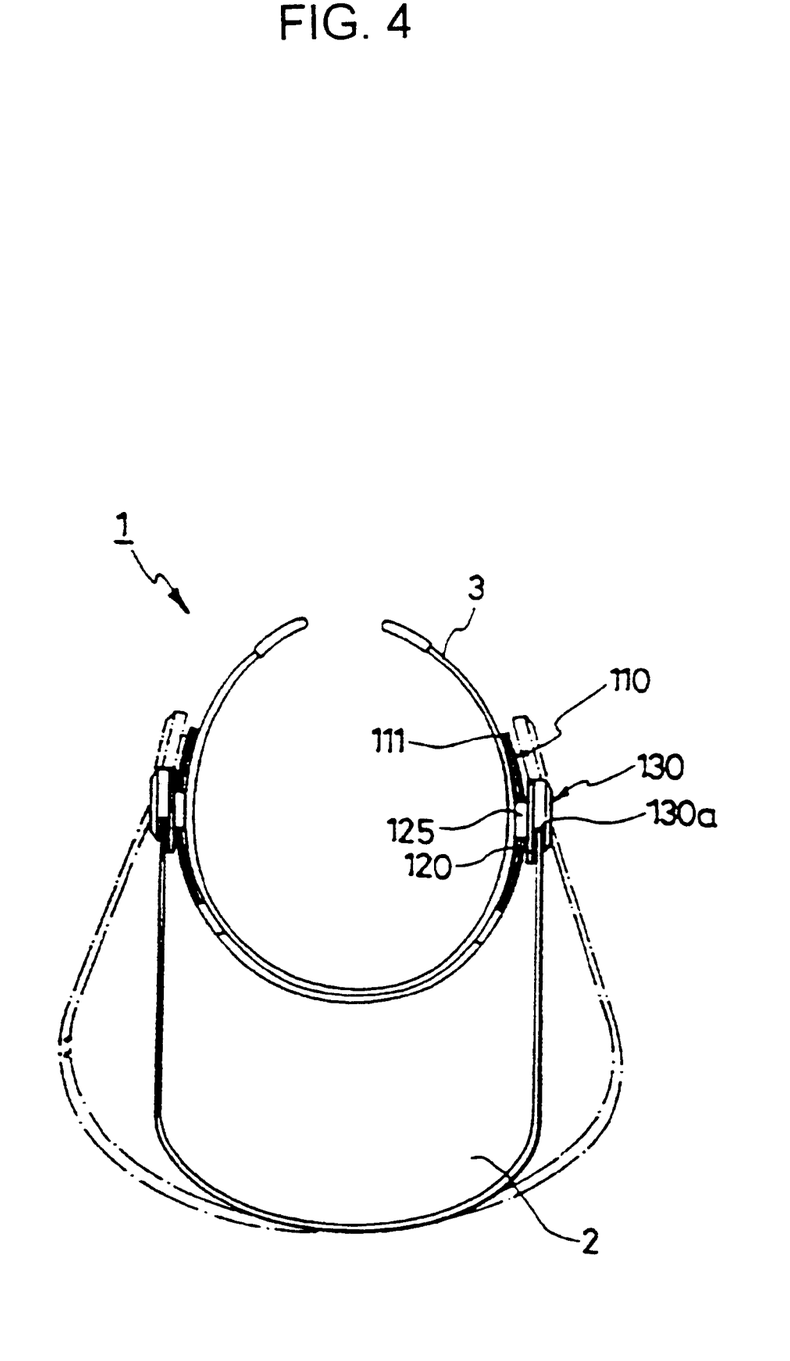
FIG. 4 is an operational view showing a horizontal rotation of a sun visor to the hat according to the present invention.
Figure 5:
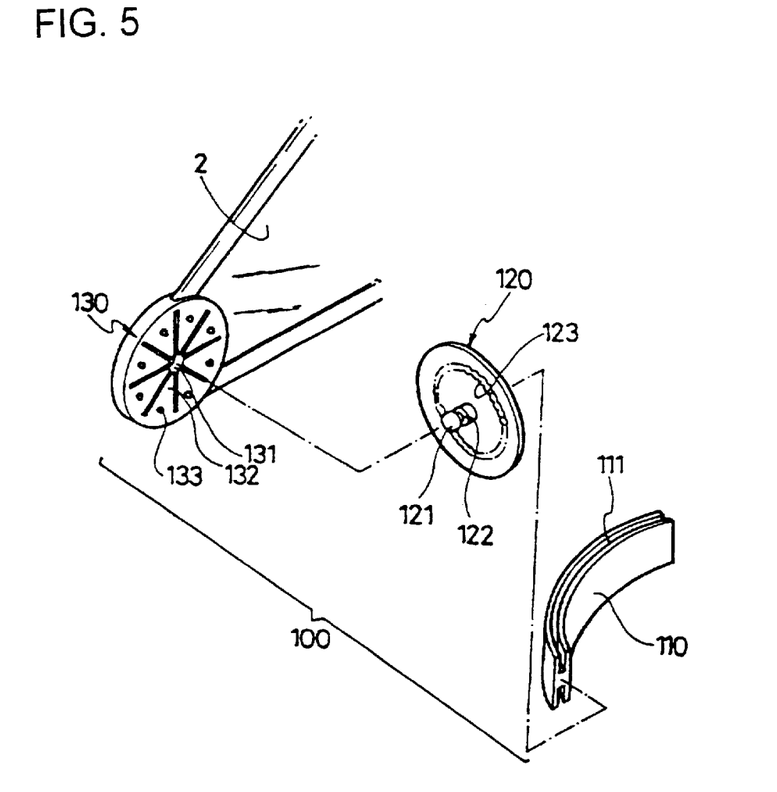
FIG. 5 is a partial view showing a rolling device according to the present invention.
Figure 6:
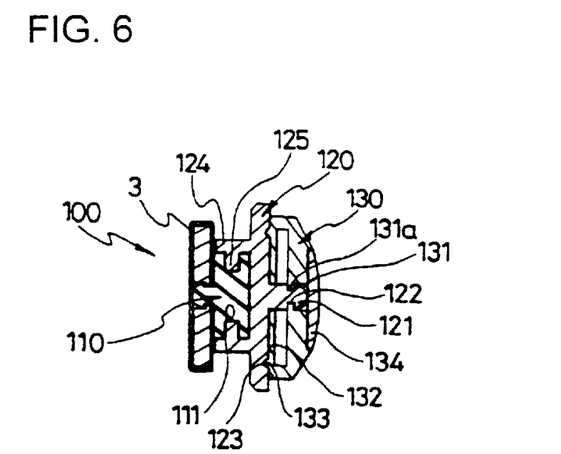
FIG. 6 is a view showing a main portion according to the present invention.
Figure 7:
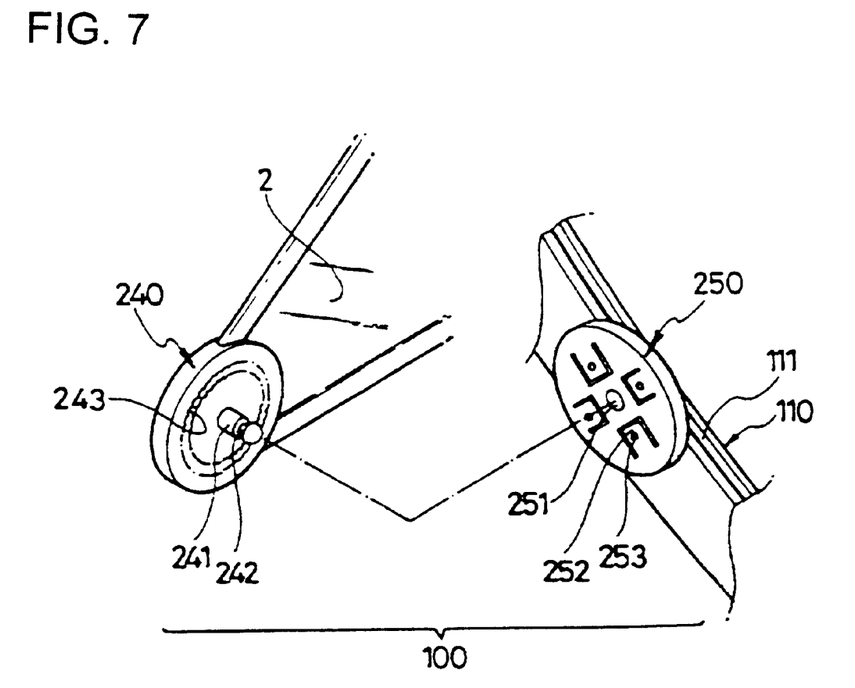
FIG. 7 is a partially exploded view showing a main portion according to the present invention.
Figure 8:
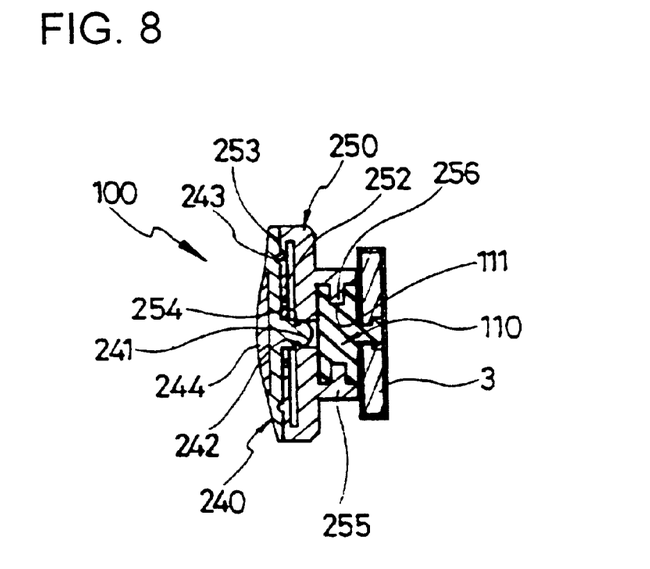
FIG. 8 is a cross-sectional assembly view of FIG. 7.

As further shown in FIGS. 7 and 8, an inner disk 250 may be formed such that an insertion hole 251 is formed in the center of the outer surface of the inner disk 250. A plurality of elastic plates 252 are radially formed from the insertion hole 251. A plurality of protrusions 253 are formed on the elastic plates 252. Also, an outer disk 240 receiving the each end of the sun visor 2 is provided for engagement to the inner disk 250. A hinge shaft 241 formed on the inner surface of the outer disk 240 becomes engaged into the insertion hole 251, whereby the sun visor 2 makes a vertical angular movement. Eventually, the sun visor 2 can be elastically adjusted for its desired angular movement. The protrusions 253 on the inner disk 250 becomes controllably engaged in the openings 243 of the outer disk 240.

Figure 9:
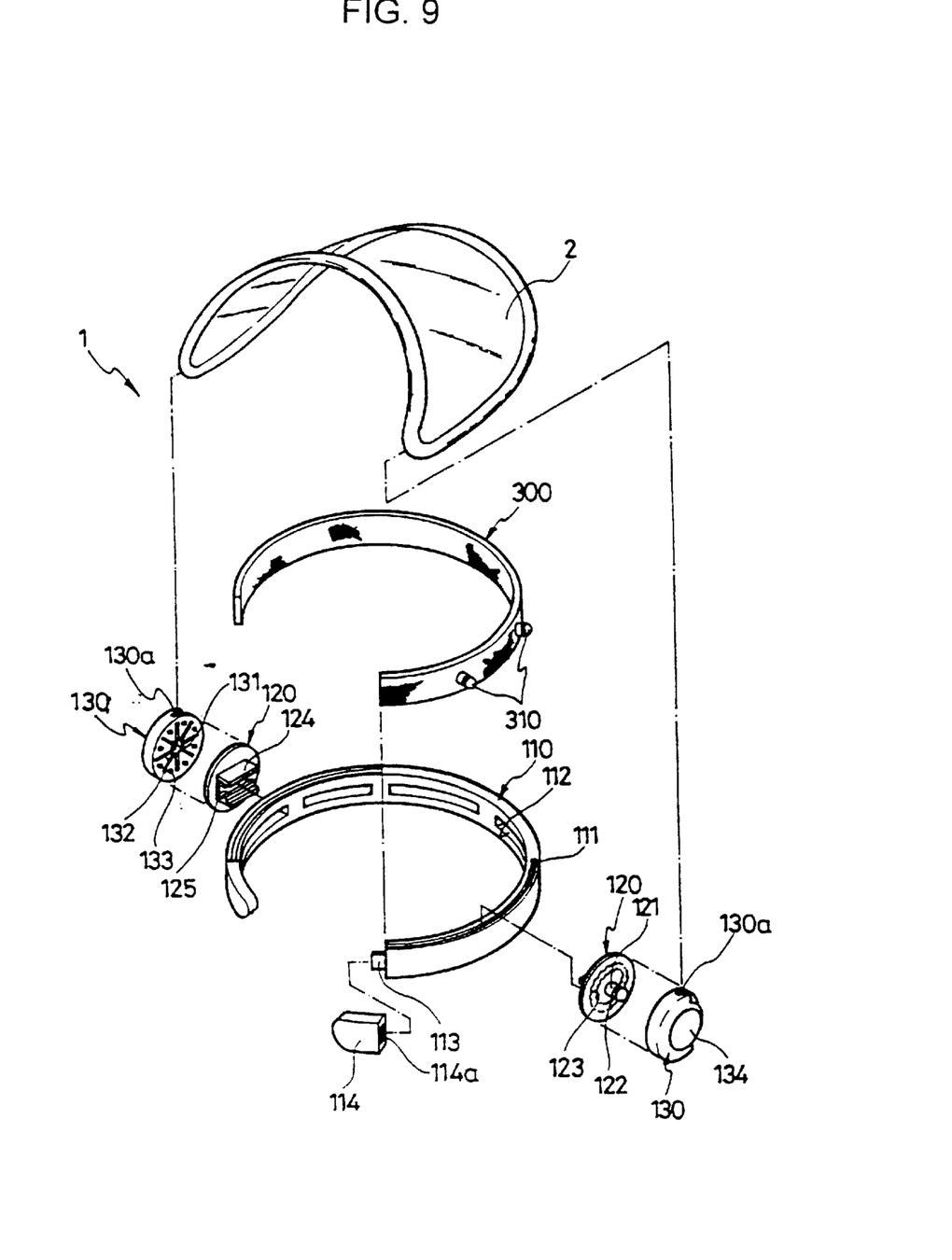
FIG. 9 is an exploded perspective view showing another embodiment of the present invention.
Figure 10:
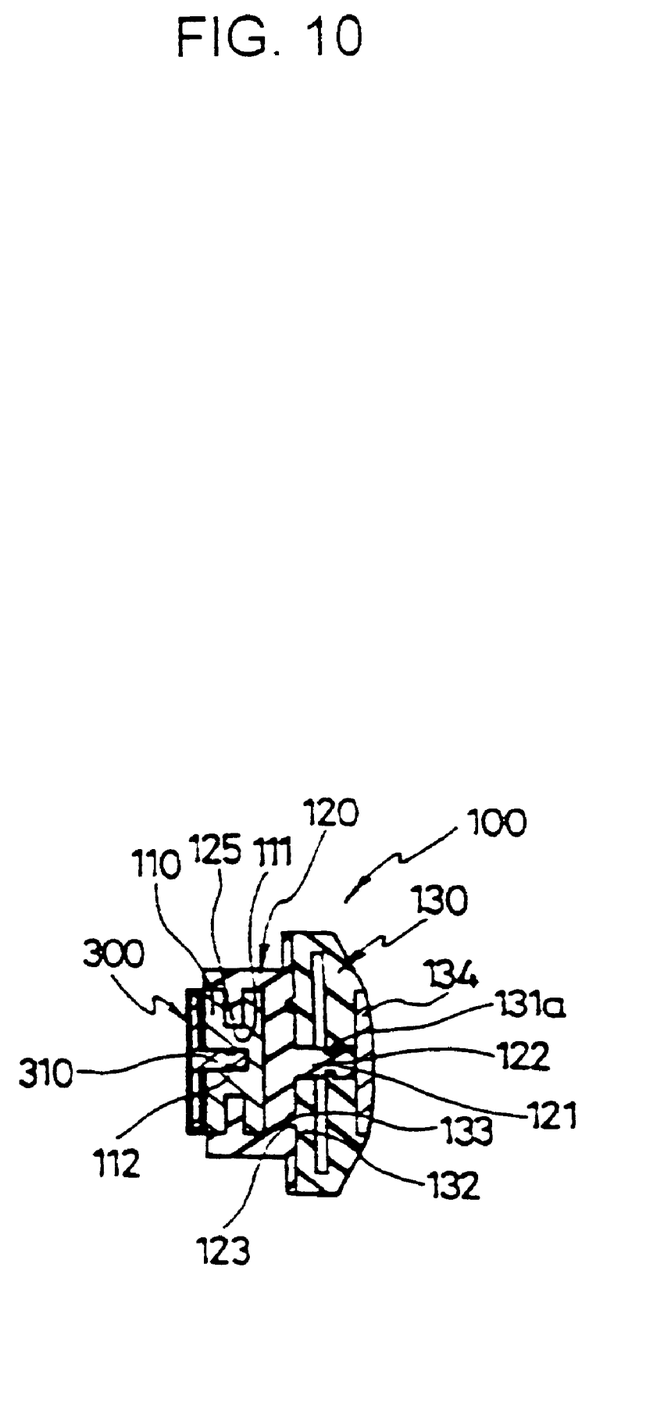
FIG. 10 is a partial assembly view of FIG. 9.

Also, as shown in FIGS. 9 and 10, the elastic band 300 may be formed identical in size to the guide support 110. That is, a plurality of lengthwise grooves 112 are formed in the inner periphery of the guide support 110, and the guide groove 111 is formed in upper and lower end portions of the guide support 110 so that the slider 124 can be controllably engaged to and guided by the guide support 110.

On each side end of the guide support 110 is formed a protrusion 113, where a cap 114 is pressed to and inserted by the protrusion 113 to improve comfortability in hat wearing.

A plurality of support protrusions 310 extend from the outer periphery of the elastic band 300 to detachably become engaged to the guide support 110. Specifically, the support protrusions 310 of the elastic band 300 are detachably engaged into the support grooves 112 of the guide support 110. Preferably, the elastic band 300 is covered by a soft fabric material for comfortable wearing.

Figure 11:
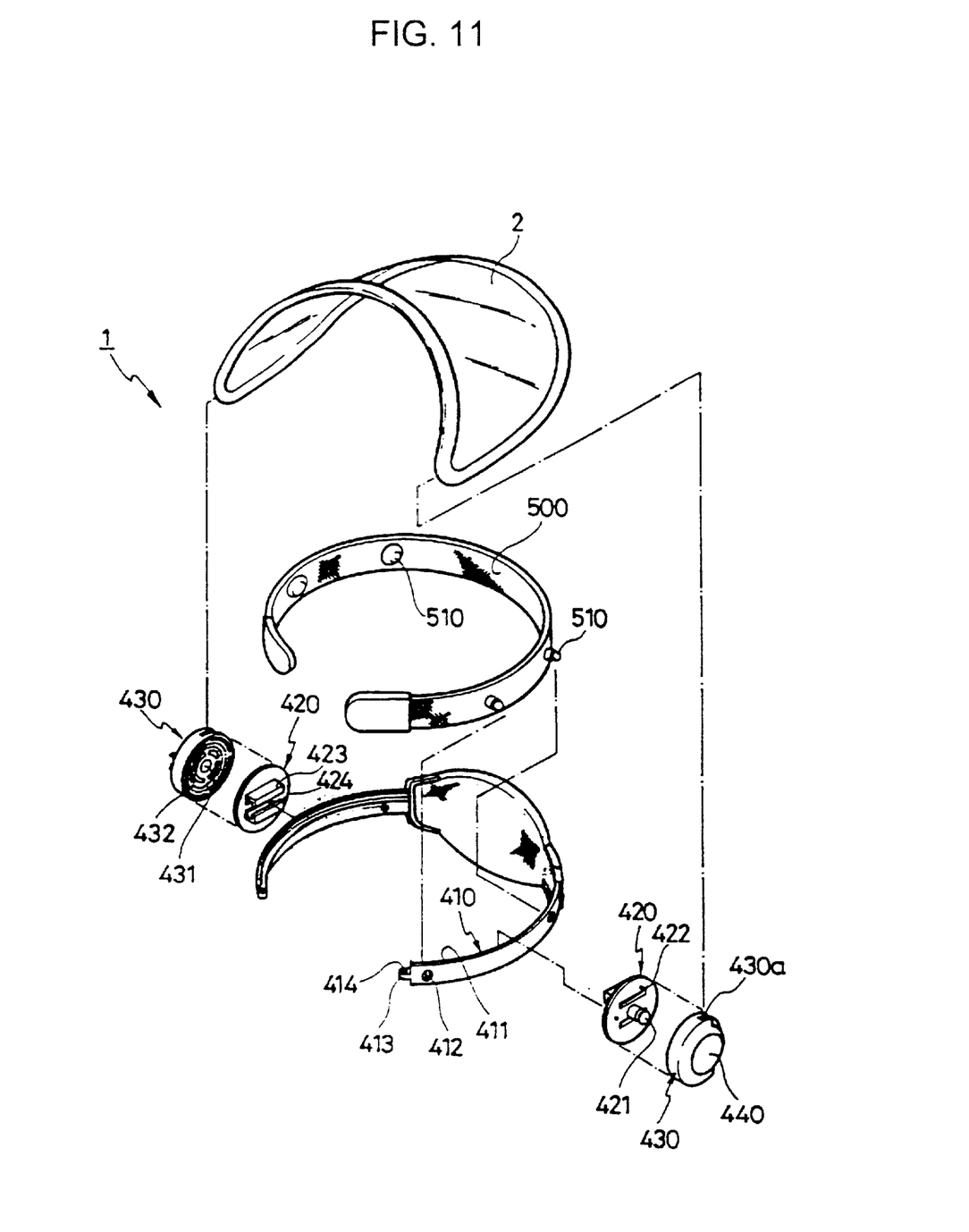
FIG. 11 is an exploded perspective view showing still another embodiment of the present invention.

With reference to FIG. 11, the elastic band 500 has a plurality of protrusions 510 spaced from each other and extending from the outer periphery thereof. The guide support 410 has a sliding rail 411 vertically extending from each of upper and lower end thereof so that the inner disk 420 can be guided thereby.

The sun visor unit 100 includes a slider 424 attached to the inner surface of the inner disk 420 so that the slider 424 can slide on the sliding rail 411 which serves to enable the sun visor 2 to make a side-to-side movement, and an inner disk 420 having three protrusions 422 on the outer surface of the inner disk 420. Here, a hinge shaft 421 extends from the outer surface of the inner disk 420.

An engagement hole 412 is formed on each side portion of the guide support 410. An insertion hole 431 is formed in the inner central surface of the outer disk 430 to enable a vertical angular movement of the sun visor 2. The closure 440 is attached to the outer surface of each outer disk 430. Also, a protrusion 413 is formed extending from each end of the guide support 410 wherein the protrusion 413 with a hole is provided to allow the hat 1 to become hanged from a user's neck using a string passing through the hole of the protrusion 413.

The operation and effect of the ultraviolet rays protecting hat 1 according to the present invention will now be described. First, in order to wear the hat 1, the user widens a little and places the elastic band 2 around the user's head. Also, in order for the user to lower or raise the sun visor 2 with the hat 1 on, the user holds and moves the sun visor 2 toward the desired direction, that is, toward an upward direction or a downward direction then each outer disk 130 makes a rotation.

The outer disk 130 makes a rotation while being supported by the hinge shaft 121 inserted into the insertion hole 131. When the outer disk 130 makes a rotation, the protrusion 133 on the elastic plates 132 makes a gradual movement along the groove 123 formed in the outer surface of the inner disk 120. At this time, the elastic plates 132 having the protrusions 133 thereon is little by little pulled toward the inner portion of the outer disk 130 whenever the protrusion 133 makes a movement.

When the outer disk 130 makes a rotation tracking the groove 123 on the inner disk 120, the feeling of the movement is transferred to the sun visor held by the user so that the user can make a minute angular adjustment of the sun visor 2. Further, since the sun visor 2 stays fixed in the opening 130a of the outer disk 130 the sun visor is not further lowered so the user may rest assured of an unexpected shading of eye vision during sports watching, fishing and the like.

Moreover, when the sun rays come askew in a state that the sun visor 2 is slanted the sun visor 2 can be turned toward the direction of sun rays. In this circumstance, the sun visor 2 moves along the guide support 110 flexibly engaged to the outer periphery of the elastic band 3.

To detail the horizontal movement of the sun visor 2, the inner disk 120 attached thereto by the outer disk 130 moves along the guide groove 111 of the guide support 110. That is, the slider 124 formed on the inner surface of the inner disk 120 makes a horizontal movement along the guide groove 111 of the guide support 110.

The slider 124 moving along the guide groove 111 tracks along the bottom of the guide groove 111 wherein the groove bottom is wavy with bossy protrusions 125a, whereby the horizontal rotation can be minutely adjusted.

As further shown in FIGS. 7 and 8, in order to lower the elastic band 3 the elastic band 3 is held and lowered so the outer disk 240 flexibly engaged to each side of the elastic band 3 is rotated in accordance therewith.

The hinge shaft 241 extending from the center of the outer surface of the outer disk 240 is rotated in the insertion hole 251 of the inner disk 250 engaged to the guide support 110. When the outer disk 240 rotates following the sun visor 2, the protrusions 253 on the elastic plates 252 of the inner disk 250 are rotatably engaged in the circularly waved groove 243 of the outer disk 240, whereby the outer disk 240 makes a controllable rotation in accordance with the manual adjustment of the sun visor 2.

Accordingly, the protrusions 253 on the elastic plates of the outer surface of the inner disk 250 proceed along the circular groove 243. At this time, the rotational movement of the outer disk 240 is felt by the user's hand so that the user can make a minute angular control of the sun visor 2.

When the protrusions on the inner disk 250 proceed along the groove 243 of the outer disk 240, the elastic plates 252 with the protrusions 253 thereon are little by little pulled in the inner disk 250.

To have the height adjusted sun visor 2 stay at the adjusted location, the sun visor 2 is left untouched then the protrusions 253 of the elastic plates 252 are fit in the groove 243 of the outer disk 240, whereby the sun visor 2 comes to maintain the location desired by the user.

Also, when the sun rays comes askew the user can rotate the sun visor 2 to the desired side to block the sun rays, wherein the slider 255 on the inner surface of the inner disk 250 moves along the guide groove 111 of the guide support 110.

At this time, when the sun visor 2 stops its horizontal rotation, the wavy protrusions 111a on the bottom of the guide groove 111 become engaged to the wavy protrusions 125a of the slider 255 so that the sun visor 2 does not make a further movement, whereby the user can maintain a stable horizontal location of the sun visor 2.

Further referring to FIGS. 9 and 10, the vertical rotational movement of the sun visor 2 is implemented by the outer disk 130 engaged to the inner disk 120 when the sun visor 2 is manually controlled by the user, and the horizontal rotational movement of the sun visor 2 is implemented by engagement of the slider 124 of the inner disk 120 and the guide groove 111 of the guide support 110 in accordance with the sidewise manual adjustment of the sun visor 2.

As discussed above, the hat 1 according to the present invention allows the elastic band 300 to be detached from the guide groove 112 of the guide support 110 to thus enable the user to maintain the hat 1 clean.

To reinstall the elastic band 300 onto the guide support 110, the protrusions 310 on the elastic band 300 are pressed into the guide groove 112 formed along the guide support 110 to stably fix the elastic band 300 to the guide support, thereby enabling the user to maintain the hat 1 clean with convenience.

As shown in FIG. 11, in an embodiment, the engagement protrusions 510 extending from the outer periphery of the elastic band 500 are inserted into the engagement holes 412 from through the guide support 410 to thereby allow the elastic band 500 and the guide support 410 to become engaged with each other.

The slider 423 on the inner disk 420 is carried on the guide rail 411 of the guide support 410 to thereby allow the guide support 410 to slide along the guide rail 411. Into the insertion hole 431 of the outer disk 430 receiving each side of the sun visor 2 is engaged the hinge shaft 421 of the inner disk 420.

The ultraviolet shielding hat 1 according to the present invention allows the user to make an angular adjustment of the sun visor 2 either horizontally or vertically. Also, as shown in FIG. 11, the weight of the hat 1 can be decreased with the provision of the thin guide support 410 and the comfortability in hat wearing can be improved by providing the elastic band 500 wrapped with a desired type of cloth.

The thin structure of the guide support 410 engaged to the elastic band 500 further satisfies esthetic demand of the user. It should also be understood that the hat type with an angularly adjustable sun visor 2 belongs to the category of the present invention.

As described above, the hat 1 according to the present invention allows the user to angularly shift the sun visor depending on the illuminant angle of the sun rays either side to side or up to down, thereby efficiently protecting the user's face from the ultraviolet rays during outdoor sport watching, fishing and the like. The hat with the adjustable sun visor may also protect the user's eyes from dusty wind during roller skating or roller blading. Especially, the angularly adjustable mechanism of the sun visor prevents the sun visor to move by itself, thereby improving product reliability.

Although the invention has been described in considerable detail with reference to certain preferred versions thereof, other versions are possible by converting the aforementioned construction. Therefore, the scope of the invention shall not be limited by the specification specified above and the appended claims.

What is claimed is:

1. An ultraviolet rays shielding hat having a sun visor, comprising:
   a) an elastically circular band having an outer periphery, wherein the outer periphery has side portions;
   b) a plurality of guide supports attached to the side portions of the outer periphery of the elastic band, wherein said each guide support has a guide groove in each of a top side and a bottom side thereof;
   c) an inner support disk having an inner surface and an outer surface, wherein a slider is attached to the inner surface of the inner support disk and has a pair of guide rails inwardly extending therefrom, wherein the guide rails are slidably carried in the guide grooves of the guide supports, wherein a guide shaft extends from a central portion of the outer surface of the inner support disk; and
   d) an outer support disk having a side engagement opening and a central engagement hole, wherein the guide shaft of the slider is rotatably engaged in the central engagement hole of the outer support disk, wherein each side end of the sun visor is fixedly received in the side engagement opening of the outer support disk.

2. The ultraviolet rays shielding hat of claim 1, wherein said each guide groove of said each guide support is formed wavy on a bottom thereof and said each guide rail of said each slider is formed wavy on an end thereof.

3. The ultraviolet rays shielding hat of claim 1, wherein a plurality of bossy protrusions are circularly provided on the outer surface of the inner support disk and regularly spaced from each other around the guide shaft, wherein a wavy groove is circularly formed in an inner surface of the outer support disk to correspond to the bossy protrusions of the inner support disk.

4. The ultraviolet rays shielding hat of claim 1, wherein an elongate guide opening is formed in the inner surface of said guide support.

5. The ultraviolet rays shielding hat of claim 1, wherein a hook protrusion having a string hole is formed extending from each end of the guide support, wherein the hook protrusion allows the hat to become hanged from the user's neck using a string passing through the string hole.

6. The ultraviolet rays shielding hat of claim 5, wherein a cap is provided to cover the hook protrusion.

7. The ultraviolet rays shielding hat of claim 1, wherein the inner surface of the outer support disk is radially divided into a plurality of pieces thereof from the insertion hole of the outer support disk to further generate elasticity when the sun visor is lowered or raised.

8. The ultraviolet rays shielding hat of claim 1, wherein the outer surface of the outer support disk is covered by a closure to esthetically protect the outer support disk.

\* \* \* \* \*